US00PP13036P2

(12) United States Plant Patent
Wain

(10) Patent No.: US PP13,036 P2
(45) Date of Patent: Oct. 1, 2002

(54) CHRYSANTHEMUM PLANT NAMED 'LITTLE FIROCK'

(75) Inventor: Peter Wain, Locksheath (GB)

(73) Assignee: Fides Goldstock Breeding B.V., Maasland (NL)

( * ) Notice: Subject to any disclaimer, the term of this patent is extended or adjusted under 35 U.S.C. 154(b) by 0 days.

(21) Appl. No.: 09/996,396

(22) Filed: Nov. 30, 2001

(51) Int. Cl.[7] ..... A01H 5/00

(52) U.S. Cl. ..... Plt./298

(58) Field of Search ..... Plt./298

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'Little Firock', characterized by its uniform and upright plant habit; strong and freely branching growth habit; dark green foliage; uniform flowering habit; eight-week response time; large daisy-type inflorescences; purple and white bi-colored ray florets; and good postproduction longevity.

1 Drawing Sheet

BOTANICAL CLASSIFICATION/CULTIVAR DENOMINATION

*Chrysanthemum×morifolium* cultivar Little Firock.

BACKGROUND OF THE INVENTION

The present Invention relates to a new and distinct cultivar of Chrysanthemum plant, botanically known as *Chrysanthemum×morifolium* and hereinafter referred to by the name 'Little Firock'.

The new Chrysanthemum is a product of a planned breeding program conducted by the Inventor in Fareham, Hampshire, United Kingdom. The objective of the breeding program is to create new potted Chrysanthemum cultivars with uniform plant growth habit, desirable inflorescence form and floret colors, and good postproduction longevity.

The new Chrysanthemum originated from a cross made by the Inventor in February, 1998, in Fareham, Hampshire, United Kingdom, of a proprietary Chrysanthemum seedling selection identified as code number 96w 4, not patented, as the female, or seed, parent with a proprietary Chrysanthemum seedling selection identified as code number 201w 1, not patented, as the male, or pollen, parent. The new Chrysanthemum was discovered and selected by the Inventor as a single flowering plant within the progeny of the stated cross grown in a controlled environment in Fareham, Hampshire, United Kingdom. The selection of this plant was based on its desirable inflorescence form and purple and white bi-colored ray florets.

Asexual reproduction of the new Chrysanthemum by vegetative tip cuttings was first conducted in Fareham, Hampshire, United Kingdom in February, 1999. Asexual reproduction by vegetative tip cuttings has shown that the unique features of this new Chrysanthemum are stable and reproduced true to type in successive generations.

SUMMARY OF THE INVENTION

The cultivar Little Firock has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Little Firock'. These characteristics in combination distinguish 'Little Firock' as a new and distinct Chrysanthemum:

1. Uniform and upright plant habit.
2. Strong and freely branching growth habit.
3. Dark green foliage.
4. Uniform flowering habit.
5. Can be grown as a disbud or spray-type.
6. Eight-week response time.
7. Large daisy-type inflorescences that are about 9.75 cm in diameter.
8. Purple and white bi-colored ray florets.
9. Good postproduction longevity with plants maintaining good substance and color for at least three weeks in an interior environment.

Plants of the new Chrysanthemum are similar to plants of the female parent selection in ray floret coloration, however plants of the new Chrysanthemum have smaller inflorescences than plants of the female parent selection.

Plants of the new Chrysanthemum differ primarily from plants of the male parent selection in ray floret coloration as plants of the new Chrysanthemum have purple and white bi-colored ray florets whereas plants of the male parent selection have purple-colored ray florets. In addition, plants of the new Chrysanthemum have larger inflorescences and flower earlier than plants of the male parent selection.

Plants of the new Chrysanthemum can be compared to plants of the cultivar Yolompoc, disclosed in U.S. Plant Pat. No. 11,203. In side-by-side comparisons conducted by the Inventor in Fareham, Hampshire, United Kingdom, plants of the new Chrysanthemum differed from plants of the cultivar Yolompoc in the following characteristics:

1. Plants of the new Chrysanthemum had larger leaves and inflorescences than plants of the cultivar Yolompoc.
2. Plants of the new Chrysanthemum had thicker and stronger stems than plants of the cultivar Yolompoc.
3. Plants of the new Chrysanthemum flowered about 5 days later than plants of the cultivar Yolompoc.

4. Plants of the new Chrysanthemum and the cultivar Yolompoc differed in ray floret coloration as plants of the new Chrysanthemum had purple and white bi-colored ray florets whereas plants of the cultivar Yolompoc had purple-colored ray florets.

Plants of the new Chrysanthemum can also be compared to plants of the cultivar Yonashville, disclosed in U.S. Plant Pat. No. 11,795. In side-by-side comparisons conducted by the Inventor in Fareham, Hampshire, United Kingdom, plants of the new Chrysanthemum differed from plants of the cultivar Yonashville in the following characteristics:

1. Plants of the new Chrysanthemum were sturdier than plants of the cultivar Yonashville.

2. Plants of the new Chrysanthemum flowered about 10 days later than plants of the cultivar Yonashville.

3. Plants of the new Chrysanthemum and the cultivar Yonashville differed in ray floret coloration as plants of the new Chrysanthemum had purple and white bi-colored ray florets whereas plants of the cultivar Yonashville had pink-colored ray florets.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the first sheet comprises a side perspective view of a typical flowering plant of 'Little Firock' grown as a disbud-type.

The photograph at the bottom of the sheet comprises a close-up view of typical inflorescences of 'Little Firock' grown as a disbud-type.

DETAILED BOTANICAL DESCRIPTION

In the following description, color references are made to The Royal Horticultural Society Colour Chart, version 1995, except where general terms of ordinary dictionary significance are used. The aforementioned photographs and following observations and measurements describe plants grown and flowered during the summer and autumn in Leamington, Ontario, Canada, in a fiberglass-covered greenhouse and under conditions which approximate those generally used in commercial potted Chrysanthemum production. Four unrooted cuttings were directly stuck in 15-cm containers, exposed to long day/short night conditions, and pinched once about 14 days later. At the time of pinching, the photoinductive short day/long night treatments were started. Plants used for this description were grown as disbud-types. Measurements and numerical values represent averages of typical flowering plants.

Botanical classification: *Chrysanthemum×morifolium* cultivar Little Firock.

Commercial classification: Daisy-type potted Chrysanthemum.

Parentage:

*Female, or seed, parent.*—Proprietary *Chrysanthemum×morifolium* seedling selection identified as code number 96w 4, not patented.

*Male, or pollen, parent.*—Proprietary *Chrysanthemum×morifolium* seedling selection identified as code number 201w 1, not patented.

Propagation:

*Type.*—Vegetative tip cuttings.

*Time to initiate roots.*—About four days at 21° C.

*Time to produce a rooted cutting.*—About ten days at 21° C.

*Root description.*—White, fibrous.

*Rooting habit.*—Freely branching.

Plant description:

*Appearance.*—Herbaceous daisy-type potted Chrysanthemum that can be grown as a disbud or as a spray-type. Stems mostly upright; uniform crown. Freely branching, about four lateral branches develop after removal of terminal apex (pinching); dense and full plants.

*Plant height.*—About 31 cm.

*Plant diameter or spread.*—About 34.5 cm.

*Lateral branches* (*peduncles*).—Length: About 26 cm. Diameter: About 4.5 mm. Internode length: About 1.6 cm. Strength: Strong. Texture: Pubescent. Color: 144A to 146A.

*Foliage description.*—Arrangement: Alternate. Length: About 5.75 cm. Width: About 4.1 cm. Apex: Cuspidate to mucronate. Base: Attenuate. Margin: Palmately lobed, sinuses between lateral lobes mostly parallel. Texture: Upper and lower surfaces with very fine pubescence; veins prominent on lower surface. Color: Young foliage, upper surface: Slightly darker than 147A. Young foliage, lower surface: Sightly darker than 147B. Fully expanded foliage, upper surface: Close to 147A. Fully expanded foliage, lower surface: Close to 147B. Venation: Upper surface: 147A. Lower surface: 147B. Petiole length: About 1.7 cm. Petiole diameter: About 5 mm. Petiole color: Upper surface: Close to 147B to 147C. Lower surface: Close to 147C.

Inflorescence description:

*Appearance.*—Daisy-type inflorescence form with elongated oblong-shaped ray florets. Inflorescences borne on terminals above foliage. Disk and ray florets arranged acropetally on a capitulum. Not fragrant. Can be grown as a disbud or spray-type. Flowering response: Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about 8 weeks later.

*Postproduction longevity.*—Inflorescences maintain good color and substance for at least three weeks in an interior environment.

*Quantity of inflorescences.*—Grown as a disbud-type, only one inflorescence, the terminal inflorescence, develops per lateral branch.

*Inflorescence bud.*—Height: About 5.5 mm. Diameter: About 7.5 mm. Color: 143A.

*Inflorescence size.*—Diameter: About 9.75 cm. Depth (height): About 2.7 cm. Diameter of disc: About 2.1 cm. Receptacle diameter: About 7.5 mm.

*Ray florets.*—Shape: Elongated-oblong. Orientation: Initially upright, then about 50° from vertical.

Aspect: Flat to slightly convex. Length: About 4.6 cm. Width: About 9 mm. Apex: Mostly acute. Base: Attenuate; short corolla tube. Corolla tube length: About 5 mm. Margin: Entire. Texture: Smooth, velvety. Number of ray florets per inflorescence: About 35 arranged in one or two rows. Color: When opening and fully expanded, upper surface: Towards apex, white, close to 155D; mid-section and base, purple, closest to 61A. Ray floret coloration does not fade with subsequent development. When opening and fully expanded, lower surface: Towards apex, white, close to 155D; mid-section and base, white, close to 155D, underlain with purple, close to 70A to 71A.

*Disc florets.*—Arrangement: Massed at center of receptacle. Shape: Tubular, elongated. Apex: Five-pointed. Length: About 7 mm. Width: Apex: About 2 mm. Base: About 1 mm. Number of disc florets per inflorescence: About 273. Color: Immature: 154A. Mature: Apex: 9A. Mid-section: 150D. Base: Close to 155D.

*Phyllaries.*—Quantity per inflorescence: About 25. Length: About 1 cm. Width, at base: About 3 mm. Shape: Elongated, linear. Apex: Acute. Base: Truncate. Texture: Upper surface, smooth; lower surface, pubescent. Color, upper and lower surfaces: 147A.

*Reproductive organs.*—Androecium: Present on disc florets only. Anther color: 9A. Pollen amount: Scarce. Pollen color: 15A. Gynoecium: Present on both ray and disc florets.

*Seed.*—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Little Firock', as illustrated and described.

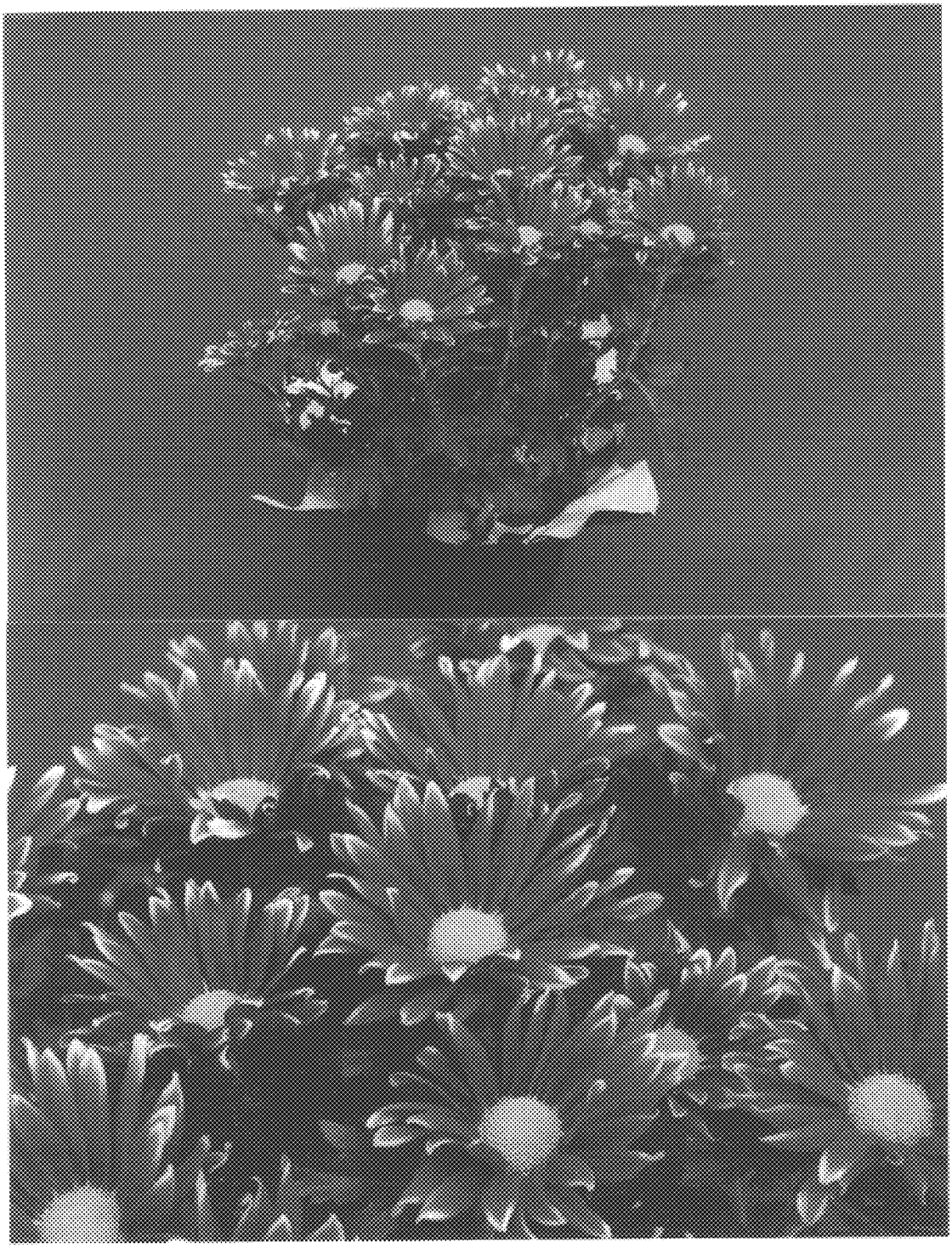

* * * * *